United States Patent [19]
Leibinsohn

[11] Patent Number: 5,102,400
[45] Date of Patent: Apr. 7, 1992

[54] DRIP CHAMBER FOR INFUSION APPARATUS

[76] Inventor: Saul Leibinsohn, 11 Olei Hagardom Street, Rishon Lezion, Israel

[21] Appl. No.: 239,725

[22] Filed: Sep. 2, 1988

Related U.S. Application Data

[63] Continuation-in-part of Ser. No. 932,861, Nov. 20, 1986, abandoned.

[30] Foreign Application Priority Data

Nov. 20, 1985 [IL] Israel ........................................ 77109

[51] Int. Cl.$^5$ ............................................. A61M 5/165
[52] U.S. Cl. ................................... 604/251; 222/464; 137/590; 604/122
[58] Field of Search ............... 604/251, 252, 254, 257, 604/260–262, 403, 405, 406, 407, 411, 122; 222/387, 454, 464; 137/123, 152, 153, 590, 591

[56] References Cited

U.S. PATENT DOCUMENTS

| | | | |
|---|---|---|---|
| 1,127,387 | 2/1915 | Alger | 222/416 |
| 3,045,872 | 7/1962 | Hronas et al. | 222/464 |
| 3,285,478 | 11/1966 | Gordon | 222/464 |
| 3,385,483 | 5/1968 | Gilwood | 222/416 |
| 3,744,492 | 7/1973 | Leibinsohn | 604/251 |
| 4,203,463 | 5/1980 | Ponlot et al. | 604/254 |

FOREIGN PATENT DOCUMENTS

| | | | |
|---|---|---|---|
| 154629 | 5/1956 | Sweden | 604/251 |
| 200318 | 12/1964 | Sweden | 604/252 |
| 2141487 | 12/1984 | United Kingdom | 137/123 |

*Primary Examiner*—Stephen C. Pellegrino
*Assistant Examiner*—Ralph A. Lewis
*Attorney, Agent, or Firm*—Benjamin J. Barish

[57] ABSTRACT

Liquid infusion apparatus comprises a drip chamber in which an outlet tube projecting into the chamber is enclosed by a cap including a side wall enclosing the upper portion of the outlet tube. The cap side wall has an inner diameter which is substantially largre than the outer diameter of the outlet tube, to thereby define a large passageway at the entrance of the outlet tube. This passageway substantially reduces the flow velocity of the liquid at its interface with the air in the drip chamber, and thereby substantially eliminates the possibility of air bubbles being trapped within the liquid fed through the outlet tube under high rates of liquid flow and under exceptionally rough handling conditions, such as when the transfusion is being administered while the patient is in a helicopter or in a land vehicle.

19 Claims, 1 Drawing Sheet

DRIP CHAMBER FOR INFUSION APPARATUS

RELATED APPLICATION

The present application is a continuation-in-part of Application Ser. No. 06/932,861 filed Nov. 20, 1986, now abandoned.

BACKGROUND OF THE INVENTION

The present invention relates to infusion apparatus, and particularly to a drip chamber used in such apparatus.

Infusion apparatus commonly includes drip chambers into which the liquid is introduced in the form of drops to enable visually monitoring the rate of flow of the infusion liquid. However, one of the dangers of using drip chambers is the possibility that the air within the drip chamber may enter the infusion liquid passing into the patient's body. This danger is particularly significant when the infusion sets are employed in the field, for example on a battlefield or during a disaster involving rough handling conditions, or when high rates of infusion are to be administered.

My U.S. Pat. No. 3,744,492 describes a drip chamber constructed particularly to prevent the entry of air bubbles into the infusion liquid under such conditions. That apparatus comprises a portable housing defining a drip chamber therein, an inlet connector leading from the upper end of the chamber for connection to a source of infusion liquid, an outlet connector leading from the lower end of the chamber for connection to an infusion device, and an outlet tube supported within the chamber with the lower end of the outlet tube leading to the outlet connector and the upper end of the outlet tube located at an intermediate portion of the chamber spaced below the inlet connector. The provision of the outlet tube projecting into the drip chamber produces a seal which, during the administration of the infusion, prevents the escape of air bubbles from the drip chamber into the infusion device even though the infusion set is shaken or inclined such that the vertical axis of its drip chamber deviates from the true vertical.

Drip chambers according to the construction of the above-described patent are satisfactory for most conditions of use, but not for field or rescue conditions. Thus, it was found that when the infusion was administered at a high rate and under exceptionally rough handling conditions, for example when subjected to rapid vibrations as might occur during the administration of the infusion liquid while the subject was being carried by a land or air vehicle (e.g., a helicopter), the rapid vibrations increased the turbulence of the infusion liquid such that there was produced, at the upper end of the outlet tube, a low pressure area or "funnel" which tended to draw into it air from the drip chamber, resulting in the entrainment of air bubbles in the infusion liquid.

Examples of other known types of liquid infusion devices are described in Ford U.S. Pat. No. 2,675,000 and Butler U.S. Pat. No. 2,729,212. The devices described in those patents, however, are not suitable for use at high flow rates and/or during the above-mentioned rough handling conditions, since if they were so used they would tend to entrain air into the administered liquid.

BRIEF SUMMARY OF THE INVENTION

An object of the present invention is to provide liquid infusion apparatus, and particularly a novel drip chamber construction, which provides additional protection against the drawing of air bubbles into the infusion liquid even when administered at high flow rates and during very rough handling conditions. Another object of the invention is to provide liquid infusion apparatus which permits quick and precise priming, and also permits infusion in any position of the drip chamber and without shaking.

According to the present invention, there is provided liquid infusion apparatus comprising a portable housing having a transparent drip chamber with means for introducing therein the infusion liquid in the form of drops to enable visually monitoring the rate of flow of the infusion liquid. The drip chamber includes a lower cylindrical section of large diameter, an upper cylindrical section of smaller diameter, and an intermediate conical section joining the lower and upper sections. The drip chamber further includes an inlet connector leading into the upper end of the chamber for connection to a source of infusion liquid, an outlet connector leading from the lower end of the chamber for connection to an infusion device, and an outlet tube supported within the chamber with the lower end of the outlet tube leading to the outlet connector and the upper end of the outlet tube located at an intermediate portion of the chamber spaced below the inlet connector.

The drip chamber still further includes a cap having a side wall closed at its upper end by an end wall and open at its lower end, and supporting means for supporting the cap over the upper end of the outlet tube, with the cap end wall spaced above the upper edge of the outlet tube, and the cap side wall enclosing the upper portion of the outlet tube and spaced therefrom. The inner diameter of the cap side wall is substantially larger than, preferably more than double, the outer diameter of the outlet tube enclosed by the cap side wall, to provide a passageway of large cross-sectional area for the infusion liquid at the lower end of the drip chamber to pass at high flow rates, but at a relatively low liquid velocity, between the cap side wall and the outlet tube into the upper end of the outlet tube and out through the outlet connector to the infusion device.

Drip chambers constructed in accordance with the foregoing features provides substantial protection against the formation of a "funnel" drawing air bubbles into the infusion liquid when the infusion is being administered at a high rate and particularly while the patient is being transported by a land or air vehicle which subjects the infusion apparatus to rapid vibrations. Thus, the provision of the cap defining the large cross-sectional area passageway around the upper end of the outlet tube very substantially increases the inlet area of the outlet tube, to thereby substantially reduce the velocity of the infusion liquid from the drip chamber into the outlet tube even at high flow rates.

Such protection against the entrainment of air bubbles into the infusion liquid under high flow rates and under rough handling conditions is not provided either in my above-cited U.S. Pat. No. 3,744,492 which does not include such a cap, or in the above-cited U.S. Pat. Nos. 2,675,000 and 2,729,212 which include a cap to define a very small passageway at the inlet of the outlet tube, and which thereby would tend to entrain air at high flow rates and/or under rough handling conditions.

According to a further important feature, the volume of the lower chamber setion from its bottom to the bottom of the cap side wall is smaller than the sum of the volumes of the upper and intermediate chamber sections, but greater than the volume of the intermediate chamber section alone. This relationship means that the level of the liquid in the drip chamber, when in its vertical position, would be within the intermediate conical section. This feature permits quick and precise priming of the drip chamber by inversion without shaking.

According to a further feature, the volume of the lower chamber section from its bottom to the bottom of the cap side wall is such that when the drip chamber is in its horizontal or any other position after priming, the cap is completely immersed in the liquid. This feature avoids the entry of air when administering the infusion liquid.

Further features and advantages will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
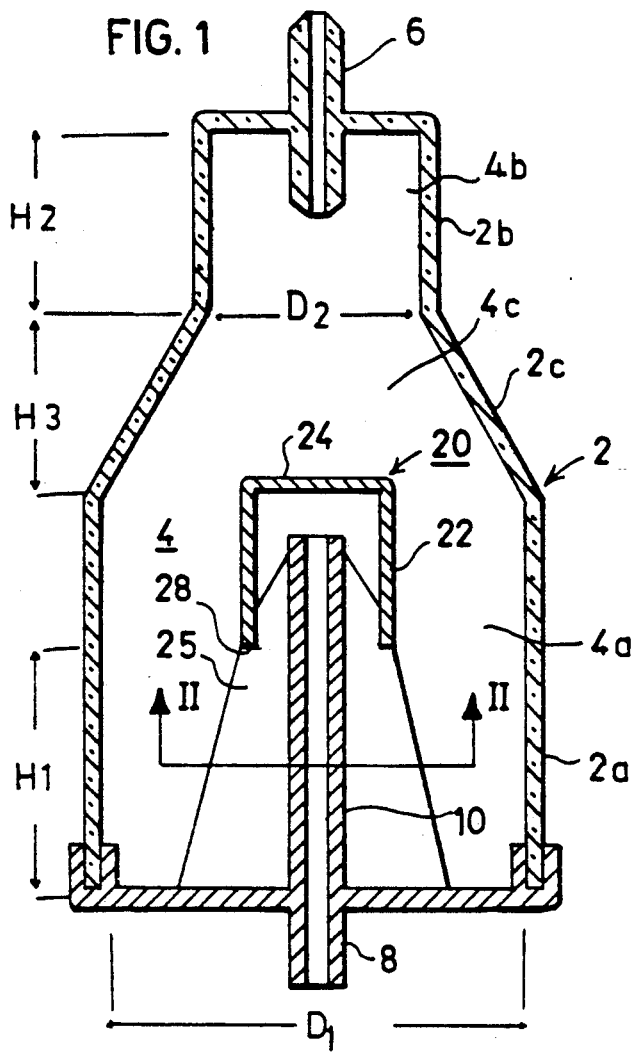
FIG. 1 is a longitudinal sectional view illustrating one form of drip chamber constructed in accordance with the present invention.
Figure 2:
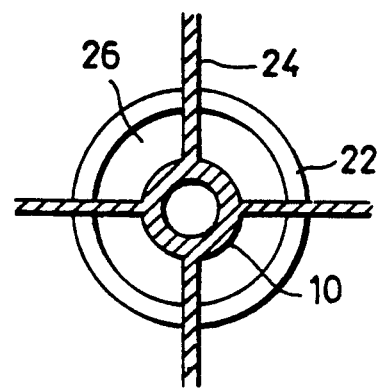
FIG. 2 is a transverse sectional view along lines II—II of FIG. 1.

The drip chamber illustrated in FIGS. 1 and 2 is of the type described in my above-cited U.S. Pat. No. 3,744,492. It includes a housing, generally designated 2, defining a chamber therein, generally designated 4. Housing 2 includes a lower cylindrical section 2a of large diameter defining a lower chamber section 4a, an upper cylindrical section 2b of smaller diameter defining an upper chamber section 4b, and an intermediate conical section 2c joining the lower and upper sections and defining a conical chamber section 4c.

The upper housing section 2b is integrally formed with an inlet connector 6 leading to the upper end of upper chamber section 4b from a source of infusion liquid, such as a suspended infusion bag (not shown); and the lower housing section 2a is integrally formed with an outlet connector 8 leading from the lower chamber section 4a for connection to an infusion device, such as a catheter or needle (not shown). An outlet tube 10 is supported within chamber section 4a with the lower end of the outlet tube leading to outlet connector 8, and the upper end of the outlet tube located at an intermediate portion of the chamber spaced below the inlet connector 6. In the example illustrated in FIG. 1, the upper end of the outlet tube is substantially at the juncture between the chamber inlet section 4a and intermediate conical section 4c.

As described in my above-cited U.S. Pat. No. 3,744,492, if the outlet tube 10 is not included, then any slight deviation of the vertical axis of the drip chamber from the true vertical is likely to expose the leading edge of the outlet connector 8 to air, such that air bubbles may pass with the infusion liquid into the patient. However, by the provision of the outlet tube 10, and also by providing the chamber lower outlet section 4a of substantially larger volume than the chamber upper inlet section 4b, the liquid accumulating within the bottom of the chamber produces a seal with respect to the inlet end of the outlet tube 10, providing protection against the escape of air bubbles into the infusion liquid during rough handling conditions of the drip chamber when it may be inclined so that its vertical axis deviates from the true vertical.

Further details of the construction and operation of the drip chamber illustrated in FIG. 1, and also a number of variations in the illustrated construction, are described in my above-cited U.S. Pat. No. 3,744,492.

As briefly mentioned above, during exceptionally rough handling conditions when the infusion is being administered at a high rate and the drip chamber is subjected to severe and rapid vibrations, such as occurring while the patient is being transported by a land or air vehicle, e.g., a helicopter, the rapid vibrations may produce a high turbulence in the infusion liquid such that under high flow rates air from the drip chamber is drawn into the infusion liquid.

In order to provide improved protection against this possibility, drip chamber illustrated in FIG. 1 is provided with a cap, generally designated 20, supported in spaced relationship with respect to the upper end of the outlet tube 10. The inner diameter of cap 20 is substantially greater than, more than double, the outer diameter of the outlet tube 10, so as to provide a large passageway from the chamber 4 into the outlet tube.

More particularly, cap 20 includes a cylindrical side wall 22 closed at its upper end by a circular end wall 24, and open at its lower end. Cap 20 is supported over the upper end of the outlet tube 10 with the cap end wall 24 spaced above the upper edge of the outlet tube, and the cap side wall 22 enclosing the upper portion of the outlet tube and spaced therefrom. This space provides a passageway of large cross-sectional area for the infusion liquid within the outlet section 4b at the lower end of the drip chamber 4 to pass between the cap side wall 22 and the outlet tube 10 into the upper end of the outlet tube, and out through the outlet connector 8 to the infusion device.

As described above, cap 20 substantially increases the area of the inlet end of the outlet tube 10. This substantially reduces the velocity and turbulence as the liquid enters the outlet tube. In this manner, the creation of a low pressure area or "funnel" is thereby prevented at the inlet end of the outlet tube, thereby providing additional protection against the drawing of air into the infusion liquid under these very rough handling conditions.

In the construction illustrated in FIGS. 1 and 2, cap 20 is supported in spaced relationship with respect to the upper end of outlet tube 10 by means of a plurality of circumferentially-spaced ribs 25 projecting radially from the outlet tube and supporting the cap. As shown particularly in FIG. 2, the spaces 26 between the ribs 25 provide the passageways for the infusion liquid to pass from the lower end of the drip chamber 4 and through the space between cap 20 and the upper portion of the outlet tube 10 in order to enter the outlet tube.

As shown particularly in FIG. 1, the plurality of ribs 25 extend axially for the complete length of the outlet tube 10. Each of the ribs 25 is of tapered configuration, being widest at the bottom and narrowest at the top, and is formed with a notch 28 at its upper end. Notches 28 of all the ribs are aligned and define an annular socket for receiving the open end of the cap side wall 22 for supporting the cap over the upper end of the outlet tube 10.

Ribs 25 may be integrally formed with the outlet tube 10; alternatively, these ribs may be integrally formed with a tubular sleeve received around the outlet tube 10.

Figure 3:
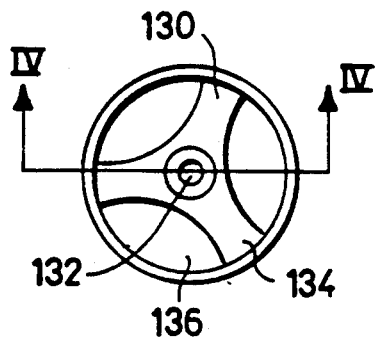
FIG. 3 is a bottom plan view illustrating a modification in the arrangement for supporting the cap in spaced relationship with respect to the upper end of the outlet tube in the drip chamber of FIGS. 1 and 2.
Figure 4:
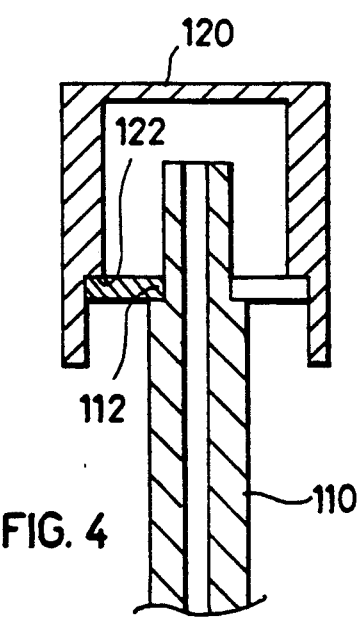
FIG. 4 is a transverse sectional view along lines IV—IV of FIG. 3.

FIGS. 3 and 4 illustrate another arrangement which may be used for supporting the cap, therein designated 120, over the upper end of the outlet tube, therein designated 110. In this arrangement, the circumferentially-spaced ribs are integrally formed in a disc, generally designated 130, received over the upper end of the outlet tube 110 and supporting the cap 120.

More particularly, the upper end of the outlet tube 110 is formed with a stepped outer face defining an annular shoulder 112 for supporting disc 130. In addition, the open end of the side wall of cap 120 is formed with a stepped inner face defining an annular shoulder 122 for receiving the outer periphery of disc 130. Disc 130 is in turn formed with a central opening 132 received on annular shoulder 112, and with three ribs 134 circumferentially-spaced from each other to define the spaces 136 which serve as the passageways for the passage of the infusion liquid from the lower end of the drip chamber into the space between cap 120 and the upper end of the outlet tube 110. The outer edges of ribs 134 lie in a circle so that they receive the annular shoulder 122 formed in the inner face of cap 120 and thus support the cap in spaced relationship over the upper end of the outlet tube 110.

It will be appreciated that in both described embodiments, the infusion liquid within the drip chamber immerses the cap (20 or 120), and that the air gap, enabling the liquid flow to be monitored, is above the upper face of the cap. Such drip chambers may be primed in the conventional manner, by opening the outlet tube (10 or 110) to the atmosphere, and then filling the chamber with the transfusion liquid until the transfusion liquid starts to exit at the outlet end of the outlet tube, thereby assuring that all the air within the outlet tube has been removed. The illustrated drip chambers, however, are preferably primed in the inverted positions.

As described above, the diameter of the inner face of the side wall of the cap (20, 120) is at least twice that of the outer face of the outlet tube (10, 110) so as to provide a passageway of large cross-sectional area for the infusion liquid to pass into the upper end of the outlet tube and out through the outlet connector to the infusion device, thereby protecting against the possibility of forming a funnel which may draw air bubbles into the outlet tube even at high flow rates and during rough handling conditions. The inner diameter of the outlet tube (10, 110) should be 2-4 mm, preferably 3 mm; the outer diameter of the outlet tube should be 3-6 mm, preferably 4 mm; the inner diameter of the cap side wall should be 8-12 mm, preferably 10 mm; and the outer diameter of the cap side wall should be 10-13 mm, preferably 11.5 mm.

In addition, the volume of the lower chamber section 4a from its bottom to the lower end of the cap side wall 22 (occupied by length $H_1$, FIG. 1) is less than the sum of the volumes of chamber sections 4b and 4c (occupied by heights $H_2$ and $H_3$), but greater than the volume of the upper chamber section 4b ($H_2$). This means that the liquid level in the drip chamber, when in its vertical position, will be within the area of the intermediate conical section 4c. This feature permits quick and precise priming by inversion without shaking. In addition, the volume of the bottom portion of chamber section 4a defined by height $H_1$ is such that when the drip chamber is in its horizontal or any other position after priming, the cap (20, 120) is completely immersed in the liquid; this avoids the entry of air when infusing. Preferably, $D_1$ should be 18-35 mm; $D_2$ should be 8-16 mm, $H_1$ should be 10-15 mm; $H_2$ should be 12-18 mm; and $H_3$ should be 6-10 mm. Particularly good results were obtained when: $D_1 = 25$ mm; $D_2 = 10$ mm; $H_1 = 12$ mm; $H_2 = 15$ mm; and $H_3 = 8$ mm.

While the invention has been described with respect to two preferred embodiments, it will be appreciated that many other variations, modifications and applications of the invention may be made.

What is claimed is:

1. Liquid infusion apparatus, comprising: a portable housing having a transparent drip chamber with means for introducing therein infusion liquid in the form of drops to enable visually monitoring the rate of flow of the infusion liquid, said drip chamber including a lower cylindrical section of larger diameter, an upper cylindrical section of smaller diameter, and an intermediate conical section joining said lower and upper sections, an inlet connector leading into the upper section of said chamber for connection to a source of infusion liquid, an outlet connector leading from the lower section of said chamber for connection to an infusion device, and an outlet tube supported within said chamber with the lower end of the outlet tube leading to said outlet connector and the upper end of said outlet tube located in the chamber spaced below said inlet connector; a cap including a side wall closed at its upper end by an end wall and open at its lower end; and supporting means for supporting said cap over the upper end of said outlet tube, with said cap end wall spaced above the upper edge of the outlet tube, and said cap side wall enclosing the upper portion of the outlet tube and spaced therefrom; the inner diameter of said cap side wall being substantially larger than the outer diameter of said outlet tube enclosed by the cap side wall, to provide a passageway of larger cross-sectional area for the infusion liquid to pass into the upper end of the outlet tube and out through said outlet connector to the infusion device, thereby protecting against the possibility of producing a funnel drawing air bubbles into the outlet tube at high flow rates and during rough handling conditions;

the volume of the lower chamber section from its bottom to the lower end of the cap side wall being smaller than the sum of the volumes of the upper and intermediate chamber sections, but greater than the volume of the upper chamber section alone.

2. The apparatus according to claim 1, wherein the inner diameter of said cap side wall is at least twice the outer diameter of said outlet tube.

3. The apparatus according to claim 1, wherein the volume of the lower chamber section section from its bottom to the bottom of the cap side wall is such that when the drip chamber is in the horizontal or any other position after priming, the cap is completely immersed in the liquid within the drip chamber.

4. The apparatus according to claim 1, wherein said supporting means comprises a plurality of circumferentially-spaced ribs projecting radially from said outlet tube and supporting said cap.

5. The apparatus according to claim 4, wherein said a plurality of ribs are formed in a disc having a central opening for receiving the upper end of said outlet tube, said cap being supported on the outer periphery of said disc.

6. The apparatus according to claim 5, wherein the upper end of said outlet tube is formed with a stepped outer face defining an annular shoulder for supporting the disc.

7. The apparatus according to claim 5, wherein the open end of said cap side wall is stepped on its inner face defining an annular shoulder for receiving the outer periphery of said disc.

8. The apparatus according to claim 4, wherein said a plurality of ribs extend axially for the complete length of said outlet tube.

9. The apparatus according to claim 8, wherein each of said ribs includes a notch at its upper end, which notches receive the open end of said cap for supporting same over said outlet tube.

10. The apparatus according to claim 8, wherein each of said ribs is of tapered configuration, being widest at the bottom and narrowest at the top.

11. The apparatus according to claim 1, wherein the outer diameter of the outlet tube is 3-6 mm, and the inner diameter of the cap side wall is 8-12 mm.

12. The apparatus according to claim 11, wherein the outer diameter of the outlet tube is 4 mm, and the inner diameter of the cap side wall is 10 mm.

13. The apparatus according to claim 1, wherein the inner diameter of the lower cylindrical section of the drip chamber is 18-35 mm.

14. Liquid infusion apparatus, comprising: a portable housing having a transparent drip chamber with means for introducing therein the infusion liquid in the form of drops to enable visually monitoring the rate of flow of the infusion liquid, said drip chamber including a lower cylindrical section of large diameter, an upper cylindrical section of smaller diameter, and an intermediate conical section joining said lower and upper sections, an inlet connector leading into the upper end of said chamber for connection to a source of infusion liquid, an outlet connector leading from the lower end of said chamber for connection to an infusion device, and an outlet tube supported within said chamber with the lower end of the outlet tube leading to said outlet connector and the upper end of said outlet tube located in the chamber spaced below said inlet connector; a cap including a side wall closed at its upper end by an end wall and open at its lower end; and supporting means for supporting said cap over the upper end of said outlet tube, with said cap end wall spaced above the upper edge of the outlet tube, and said cap side wall enclosing the upper portion of the outlet tube and spaced therefrom; the inner diameter of said cap side wall being at least twice the outer diameter of said outlet tube enclosed by said cap side wall to provide a passageway having a large cross-sectional area for the infusion liquid to pass, at high flow rates but at a relatively low liquid velocity, between the cap side wall and the outlet tube into the upper end of the outlet tube and out through said outlet connector to the infusion device, thereby protecting against the possibility of producing a funnel drawing air bubbles into the outlet tube even at high flow rates, the volume of said lower chamber section from its bottom to the bottom of the cap side wall being smaller than the sum of the volumes of the upper and intermediate chamber sections, but greater than the volume of the upper chamber section.

15. The apparatus according to claim 14, wherein said supporting means comprises a plurality of circumferentially-spaced ribs projecting radially from said outlet tube and supporting said cap.

16. The apparatus according to claim 15, wherein said plurality of ribs extend axially for the complete length of said outlet tube.

17. The apparatus according to claim 16, wherein each of said ribs includes a notch at its upper end, which notches receive the open end of said cap for supporting same over said outlet tube.

18. The apparatus according to claim 16, wherein each of said ribs is of tapered configuration, being widest at the bottom and narrowest at the top.

19. The apparatus according to claim 16, wherein said plurality of ribs are formed in a disc having a central opening for receiving the upper end of said outlet tube, said cap being supported on the outer periphery of said disc.

* * * * *